(12) United States Patent  (10) Patent No.: US 7,806,855 B2
Kliegman et al.  (45) Date of Patent: Oct. 5, 2010

(54) MANUAL BREAST PUMP (75) Inventors: Adriana B. Kliegman, New York, NY (US); Diana Sierra, Hackensack, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 11/786,235

(22) Filed: Apr. 11, 2007

(65) Prior Publication Data

US 2008/0208115 A1  Aug. 28, 2008

Related U.S. Application Data (60) Provisional application No. 60/791,156, filed on Apr. 11, 2006.

(51) Int. Cl.
*A61M 1/06* (2006.01)
(52) U.S. Cl. .......................................... 604/74; 604/73
(58) Field of Classification Search ............... 604/73–76
See application file for complete search history.

(56) References Cited

U.S. PATENT DOCUMENTS

| 11,135 | A | 6/1854 | Needham | 604/74 |
| 361,910 | A | 4/1887 | Tutton | 366/332 |
| 420,195 | A | 1/1890 | Graves et al. | 604/76 |
| 790,051 | A | 5/1905 | Halstead | 604/74 |
| 793,940 | A | 7/1905 | Kramer et al. | 119/14.16 |
| 897,289 | A | 9/1908 | Howell | 604/74 |
| 1,484,874 | A | 2/1924 | Del Castillo | 604/74 |
| 1,509,226 | A | 9/1924 | Brown | 604/74 |
| 2,160,651 | A | 5/1939 | Erling | 31/69 |
| 2,208,089 | A | 7/1940 | Von Grolman | 264/297.7 |

(Continued)

FOREIGN PATENT DOCUMENTS

DE  2807646  8/1978

(Continued)

OTHER PUBLICATIONS

International Search Report based on PCT US07/08782, dated Sep. 12, 2008.

(Continued)

*Primary Examiner*—Nicholas D Lucchesi
*Assistant Examiner*—Quynh-Nhu H Vu
(74) *Attorney, Agent, or Firm*—Ohlandt, Greeley, Ruggiero & Perle, L.L.P.

(57) ABSTRACT

A manual breast pump, including a housing; a funnel connected to the housing and forming a passage for breast milk; a cup for receiving a breast; a lid connected to an upper portion of the housing; a handle assembly connected to the lid; a substantially semi-circular finger grip connected to the housing; a piston movably connected to the handle assembly and reciprocally movable within the housing to create a negative pressure for the expression of breast milk from the breast; a flexible insert sealably secured to the cup and forming an isolated air volume between the cup and the flexible insert. A valve is removably connected to a lower portion of the housing; and a receptacle for receiving the breast milk, the receptacle being removably attached to a lower portion of the housing. The isolated air volume expands and contracts as the piston moves reciprocally within the housing, causing the flexible insert to move.

25 Claims, 8 Drawing Sheets

U.S. PATENT DOCUMENTS

| | | | |
|---|---|---|---|
| 2,346,841 A | 4/1944 | Henderson | 19/22 |
| 2,419,795 A | 4/1947 | Saunders | 128/297 |
| 2,542,505 A | 2/1951 | Gascoigne | 128/281 |
| 2,584,435 A | 2/1952 | Doerr | 257/10 |
| 2,612,136 A | 9/1952 | Davis | 119/14.52 |
| 2,696,193 A | 12/1954 | Domingo | 119/14.01 |
| 2,809,607 A | 10/1957 | Golay | 119/14.41 |
| 3,382,867 A | 5/1968 | Reaves | 128/38 |
| 3,620,408 A | 11/1971 | Holbrook et al. | 220/60 |
| 3,699,815 A | 10/1972 | Holbrook | 73/427 |
| 3,738,363 A | 6/1973 | Lunas et al. | 128/281 |
| 3,741,161 A | 6/1973 | Zhuk et al. | 119/14.36 |
| 3,782,385 A | 1/1974 | Loyd | 604/74 |
| 3,822,703 A | 7/1974 | Davisson | 604/72 |
| 3,911,920 A | 10/1975 | Susinn | 128/281 |
| 3,977,405 A | 8/1976 | Yanase | 128/281 |
| 4,041,904 A | 8/1977 | Yang | 119/14.41 |
| D251,015 S | 2/1979 | Cone | D24/23 |
| 4,249,481 A | 2/1981 | Adams | 119/14.02 |
| 4,263,912 A | 4/1981 | Adams | 128/281 |
| 4,280,445 A | 7/1981 | Phillips | 119/14.02 |
| 4,311,141 A | 1/1982 | Diamond | 128/281 |
| 4,323,067 A | 4/1982 | Adams | 128/281 |
| 4,501,585 A | 2/1985 | Friedman | 604/346 |
| 4,573,969 A | 3/1986 | Schlensog et al. | 604/74 |
| 4,583,970 A | 4/1986 | Kirchner | 604/74 |
| D283,732 S | 5/1986 | Elliott | D24/23 |
| 4,607,596 A | 8/1986 | Whittlestone et al. | 119/14.02 |
| D288,004 S | 1/1987 | Blachly | D24/109 |
| 4,673,388 A | 6/1987 | Schlensog et al. | 604/74 |
| 4,680,028 A | 7/1987 | Stuart | 604/74 |
| 4,705,504 A | 11/1987 | Viers | 604/75 |
| 4,740,196 A | 4/1988 | Powell | 604/75 |
| 4,754,776 A | 7/1988 | McKee | 137/102 |
| 4,759,747 A | 7/1988 | Aida et al. | 604/74 |
| 4,761,160 A | 8/1988 | Vermillion | 604/76 |
| 4,772,262 A | 9/1988 | Grant et al. | 604/74 |
| 4,774,874 A | 10/1988 | Adahan | 92/59 |
| 4,794,915 A | 1/1989 | Larsson | 604/75 |
| 4,796,758 A | 1/1989 | Hauk | 206/545 |
| 4,799,922 A | 1/1989 | Beer et al. | 604/74 |
| 4,813,932 A | 3/1989 | Hobbs | 604/74 |
| 4,857,051 A | 8/1989 | Larsson | 604/74 |
| 4,883,464 A | 11/1989 | Morifuki | 604/74 |
| 4,886,494 A | 12/1989 | Morifuji | 604/74 |
| 4,892,517 A | 1/1990 | Yuan et al. | 604/74 |
| 4,929,229 A | 5/1990 | Larsson | 604/74 |
| D309,500 S | 7/1990 | Yuan et al. | D24/51 |
| 4,950,236 A | 8/1990 | Wilson | 604/74 |
| 4,961,726 A | 10/1990 | Richter | 604/74 |
| 4,964,851 A | 10/1990 | Larsson | 604/74 |
| D313,103 S | 12/1990 | Kawano | D24/51 |
| 5,007,899 A | 4/1991 | Larsson | 604/74 |
| 5,009,638 A | 4/1991 | Riedweg et al. | 604/74 |
| 5,049,126 A | 9/1991 | Larsson | 604/74 |
| 5,071,403 A | 12/1991 | Larsson | 604/74 |
| 5,100,406 A | 3/1992 | Panchula | 606/74 |
| 5,161,482 A | 11/1992 | Griffin | 119/14.02 |
| 5,178,095 A | 1/1993 | Mein | 119/14.47 |
| D345,209 S | 3/1994 | Shoda et al. | D24/109 |
| 5,295,957 A | 3/1994 | Aida et al. | 604/74 |
| 5,304,129 A | 4/1994 | Forgach | 604/74 |
| 5,308,321 A | 5/1994 | Castro | 604/74 |
| 5,358,476 A | 10/1994 | Wilson | 604/74 |
| 5,415,632 A | 5/1995 | Samson | 604/74 |
| 5,474,193 A | 12/1995 | Larsson et al. | 215/11.4 |
| 5,514,166 A | 5/1996 | Silver et al. | 604/74 |
| D372,975 S | 8/1996 | Meyers et al. | D24/109 |
| 5,542,921 A | 8/1996 | Meyers et al. | 604/74 |
| D375,357 S | 11/1996 | Silver | D24/129 |
| 5,571,084 A | 11/1996 | Palmer | 604/74 |
| 5,575,768 A | 11/1996 | Lockridge et al. | 604/74 |
| 5,601,531 A | 2/1997 | Silver | 604/74 |
| 5,616,125 A | 4/1997 | Jelks | 604/74 |
| 5,638,976 A * | 6/1997 | Arnold | 220/298 |
| D383,536 S | 9/1997 | Bachman et al. | D24/109 |
| 5,720,722 A | 2/1998 | Lockridge | 604/74 |
| 5,749,850 A | 5/1998 | Williams et al. | 604/74 |
| 5,776,098 A | 7/1998 | Silver et al. | 604/74 |
| 5,797,875 A | 8/1998 | Silver | 604/74 |
| 5,810,772 A | 9/1998 | Niederberger | 604/74 |
| 5,843,029 A | 12/1998 | Bachman et al. | 604/74 |
| 5,871,456 A | 2/1999 | Armstrong et al. | 601/14 |
| 5,885,246 A | 3/1999 | Ford | 604/74 |
| D408,528 S | 4/1999 | Kan | D24/109 |
| 5,897,580 A | 4/1999 | Silver | 607/108 |
| 5,902,267 A | 5/1999 | Medo | 604/74 |
| 5,941,847 A | 8/1999 | Huber et al. | 604/74 |
| 5,947,923 A | 9/1999 | Uehara et al. | 604/74 |
| 5,954,690 A | 9/1999 | Larsson | 604/74 |
| 5,971,952 A | 10/1999 | Medo | 604/74 |
| 5,992,347 A | 11/1999 | Innings et al. | 119/14.07 |
| 6,004,186 A | 12/1999 | Penny | 450/36 |
| 6,004,288 A | 12/1999 | Hochstedler et al. | 604/74 |
| D418,598 S | 1/2000 | Jauch | D24/109 |
| D420,443 S | 2/2000 | Morifuji | D24/109 |
| 6,042,560 A | 3/2000 | Niederberger | 604/74 |
| 6,045,529 A | 4/2000 | Nüesch | 604/74 |
| 6,050,432 A | 4/2000 | Koehnke | 215/11.3 |
| 6,056,730 A | 5/2000 | Greter | 604/319 |
| 6,090,065 A | 7/2000 | Giles | 604/74 |
| 6,093,168 A | 7/2000 | Mendenhall | 604/74 |
| 6,109,100 A | 8/2000 | Buckley et al. | 73/198 |
| 6,110,140 A | 8/2000 | Silver | 604/74 |
| 6,110,141 A | 8/2000 | Nüesch | 604/74 |
| 6,139,521 A | 10/2000 | Larsson | 604/74 |
| 6,149,395 A | 11/2000 | Richter | 417/182 |
| 6,152,896 A | 11/2000 | Bachman et al. | 604/74 |
| 6,210,360 B1 | 4/2001 | Kong | 604/73 |
| 6,213,840 B1 | 4/2001 | Han | 450/36 |
| 6,227,936 B1 | 5/2001 | Mendoza | 450/36 |
| 6,257,847 B1 | 7/2001 | Silver et al. | 417/415 |
| D446,300 S | 8/2001 | Kirchner | D24/109 |
| D446,852 S | 8/2001 | Johansen et al. | D24/109 |
| D446,853 S | 8/2001 | Johansen et al. | D24/109 |
| 6,270,474 B1 | 8/2001 | Nüesch | 604/74 |
| 6,273,868 B1 | 8/2001 | Nordvik | 604/74 |
| 6,287,521 B1 | 9/2001 | Quay et al. | 422/101 |
| 6,290,671 B1 | 9/2001 | Niederberger | 604/74 |
| 6,299,594 B1 | 10/2001 | Silver | 604/74 |
| 6,328,082 B1 | 12/2001 | Lafond | 141/313 |
| 6,355,012 B1 | 3/2002 | Nüesch | 604/74 |
| 6,358,226 B1 | 3/2002 | Ryan | 604/74 |
| 6,379,327 B2 | 4/2002 | Lundy | 604/74 |
| D456,897 S | 5/2002 | Atkin et al. | D23/347 |
| 6,383,163 B1 | 5/2002 | Kelly et al. | 604/74 |
| 6,383,164 B1 | 5/2002 | Johansen et al. | 604/74 |
| 6,387,072 B1 | 5/2002 | Larsson et al. | 604/74 |
| 6,423,030 B1 | 7/2002 | Silver | 604/74 |
| 6,440,100 B1 | 8/2002 | Prentiss | 604/74 |
| 6,461,324 B1 * | 10/2002 | Schlensog | 604/74 |
| 6,481,986 B1 | 11/2002 | Silver et al. | 417/441 |
| 6,497,677 B2 | 12/2002 | Silver | 604/74 |
| 6,500,143 B2 | 12/2002 | Suh | 604/73 |
| 6,517,513 B1 | 2/2003 | Covington et al. | 604/74 |
| 6,547,756 B1 | 4/2003 | Greter et al. | 604/74 |
| 6,579,258 B1 | 6/2003 | Atkin et al. | 604/74 |
| 6,585,686 B2 | 7/2003 | Cloud | 604/74 |
| 6,663,587 B2 | 12/2003 | Silver et al. | 604/74 |
| 6,673,037 B1 | 1/2004 | Silver | 604/74 |
| 6,706,012 B2 | 3/2004 | McKendry et al. | 604/74 |
| 6,749,582 B2 | 6/2004 | Britto et al. | 604/74 |
| D496,097 S | 9/2004 | Rosnak et al. | D5/39 |
| D500,551 S | 1/2005 | Lantz et al. | D23/345 |

| | | | |
|---|---|---|---|
| 6,840,918 B1 * | 1/2005 | Britto et al. | 604/74 |
| 6,887,210 B2 | 5/2005 | Quay | 600/573 |
| 6,887,218 B2 | 5/2005 | Warburton | 604/74 |
| 6,974,440 B2 | 12/2005 | Silver | 604/74 |
| 2001/0016708 A1 | 8/2001 | Kong et al. | 604/152 |
| 2001/0038799 A1 | 11/2001 | Silver et al. | 417/515 |
| 2001/0044593 A1 | 11/2001 | Lundy | 604/74 |
| 2001/0047148 A1 | 11/2001 | Suh | 604/74 |
| 2002/0004642 A1 | 1/2002 | Cloud | 604/74 |
| 2002/0032404 A1 | 3/2002 | Silver | 604/74 |
| 2002/0033199 A1 | 3/2002 | Lafond | 141/10 |
| 2002/0072701 A1 | 6/2002 | Nuesch | 604/74 |
| 2002/0072702 A1 | 6/2002 | Quay | 604/74 |
| 2002/0127580 A1 | 9/2002 | Quay | 435/6 |
| 2002/0156419 A1 | 10/2002 | Silver et al. | 604/74 |
| 2002/0170935 A1 | 11/2002 | Annis | 224/653 |
| 2002/0193731 A1 | 12/2002 | Myers et al. | 604/74 |
| 2002/0198489 A1 | 12/2002 | Silver et al. | 604/74 |
| 2003/0004459 A1 | 1/2003 | McKendry et al. | 604/74 |
| 2003/0040734 A1 | 2/2003 | Morton et al. | 604/514 |
| 2003/0066842 A1 * | 4/2003 | Aiken et al. | 222/1 |
| 2003/0069536 A1 | 4/2003 | Greter et al. | 604/74 |
| 2003/0073951 A1 | 4/2003 | Morton et al. | 604/74 |
| 2003/0150890 A1 | 8/2003 | Perricone | 224/148.6 |
| 2003/0153869 A1 | 8/2003 | Ytteborg | 604/74 |
| 2003/0191432 A1 | 10/2003 | Silver | 604/74 |
| 2003/0191433 A1 | 10/2003 | Prentiss | 604/74 |
| 2003/0204164 A1 | 10/2003 | Britto et al. | 604/74 |
| 2004/0024351 A1 | 2/2004 | Greter et al. | 604/74 |
| 2004/0029486 A1 | 2/2004 | Greter et al. | 450/39 |
| 2004/0039330 A1 | 2/2004 | Silver | 604/74 |
| 2004/0087898 A1 | 5/2004 | Weniger | 604/74 |
| 2004/0249340 A1 * | 12/2004 | Britto et al. | 604/74 |
| 2005/0015045 A1 | 1/2005 | Tashiro et al. | 604/74 |
| 2005/0101908 A1 | 5/2005 | Atkin et al. | 604/74 |
| 2005/0154348 A1 * | 7/2005 | Lantz et al. | 604/74 |
| 2005/0154349 A1 * | 7/2005 | Renz et al. | 604/74 |
| 2005/0159701 A1 | 7/2005 | Conaway | 604/74 |
| 2005/0165350 A1 | 7/2005 | Greter et al. | 604/74 |
| 2005/0222536 A1 | 10/2005 | Silver | 604/74 |
| 2005/0234370 A1 | 10/2005 | Beal et al. | |
| 2005/0245860 A1 | 11/2005 | Britto et al. | 604/74 |
| 2005/0256449 A1 | 11/2005 | Tashiro | |
| 2006/0025718 A1 | 2/2006 | Ostrowski | 604/74 |
| 2006/0111664 A1 * | 5/2006 | Samson et al. | 604/74 |
| 2006/0173734 A1 * | 8/2006 | Brandt | 705/14 |
| 2007/0060873 A1 * | 3/2007 | Hiraoka et al. | 604/74 |

FOREIGN PATENT DOCUMENTS

| | | |
|---|---|---|
| DE | 10125160 | 12/2002 |
| EP | 0198469 | 10/1986 |
| EP | 0466462 | 1/1992 |
| EP | 1502610 | 2/2005 |
| GB | 2127293 | 4/1984 |
| GB | 2138686 | 10/1984 |
| JP | A-2001-9024 | 1/2001 |
| JP | A-2002-336347 | 11/2002 |
| WO | WO8100003 | 11/1981 |
| WO | WO8807385 | 10/1988 |
| WO | WO97/05913 | 2/1997 |
| WO | WO 99/44650 | 9/1999 |
| WO | WO0134226 | 5/2001 |
| WO | WO03013628 | 2/2003 |
| WO | WO04000390 | 12/2003 |

OTHER PUBLICATIONS

Written Opinion based on PCT US07/08782, dated Sep. 12, 2008.

* cited by examiner

MANUAL BREAST PUMP

CROSS-REFERENCE TO RELATED APPLICATION

This application claims the benefit of U.S. Provisional Application No. 60/791,156, filed Apr. 11, 2006.

BACKGROUND OF THE INVENTION

1. Field of the Invention

The present invention relates to devices and methods to obtain breast milk. More particularly, the present invention relates to a device and method for expressing breast milk through use of a breast cup and manual pump.

2. Description of the Related Art

Breast pump systems that use either manual or automatic means for obtaining breast milk are known in the art. Typically, these systems use a vacuum source to generate a negative pressure through a hood or cup that is applied to the breast.

Previous manual breast pump systems do not provide sufficient comfort and ease of use. Previous pumps have pump handles that are not ergonomically designed to fit a woman's hand, especially those women with small hands. Previous breast pump designs often require the woman to extend her hand in an uncomfortable manner. After repeated cycles of pumping, such designs can result in prolonged discomfort and lingering pain in the user's hand. Previous manual breast pump systems further fail to facilitate cleaning of the devices through use of easily separable components.

Additionally, previous manual breast pumps often create excess noise and vibrations that are annoying to a user, may cause further discomfort, and prevent the user from using the breast pump discretely.

SUMMARY OF THE INVENTION

The present disclosure provides a manual breast pump that is ergonomically designed to provide comfort and ease of use.

The manual breast pump of the present disclosure includes a housing, a funnel for connection to the housing and for forming a passage for breast milk; a cup for receiving a breast with the cup being connected to the funnel; a lid connected to an upper portion of the housing; a handle assembly connected to the lid; a substantially semi-circular finger grip attached to the housing; a piston movably secured to the handle assembly and reciprocally movable within the housing to create a negative pressure for the expression of breast milk from the breast; and a flexible insert sealably secured to the cup and forming an isolated air volume between the cup and the flexible insert. The isolated air volume expands and contracts as the piston moves reciprocally within the housing, causing the flexible insert to move. The manual breast pump also includes a valve removably connected to a lower portion of the housing; and a receptacle for receiving the breast milk. The receptacle is removably connected to a lower portion of the housing.

A method for producing a massaging action on a breast to assist in the expression of breast milk while using a breast pump is also provided. The breast pump includes a housing, a cup, a flexible insert, and a pressure source. The method comprises: forming an isolated air volume between the flexible insert and the cup, and using the pressure source to reciprocally apply and release a negative pressure within the housing. The application of the negative pressure causes the isolated air volume to expand and the flexible member to move toward the breast and apply a massaging action, and the release of the negative pressure causes the isolated air volume to contract and move away from the breast.

The present disclosure further provides a manual breast pump that avoids excessive noise and vibrations.

These and other advantages and benefits are provided by the manual breast pump of the present disclosure.

DETAILED DESCRIPTION OF EMBODIMENTS

Figure 1:
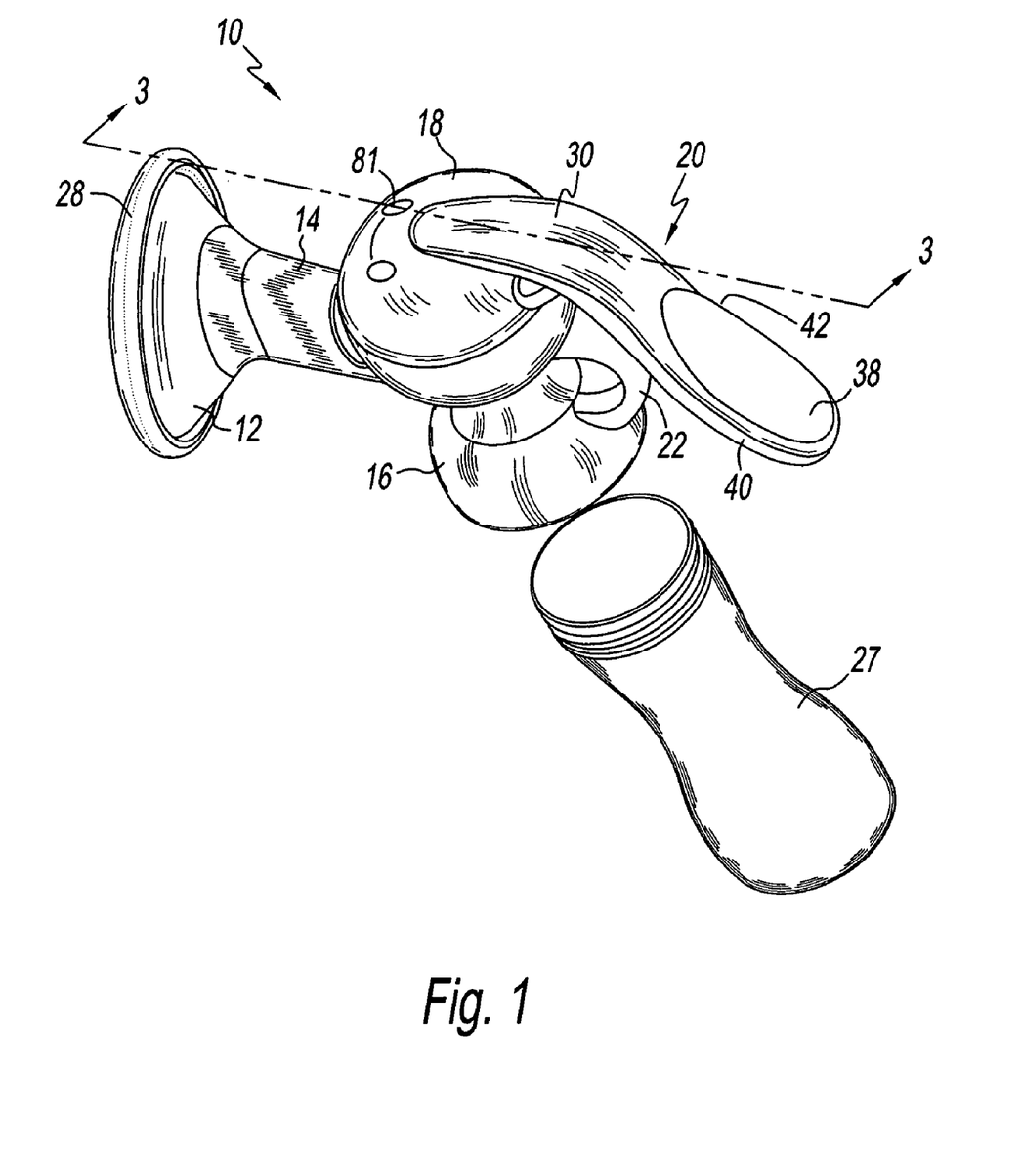
FIG. 1 is a perspective view of an exemplary embodiment of the manual breast pump described in the present disclosure.
Figure 2:
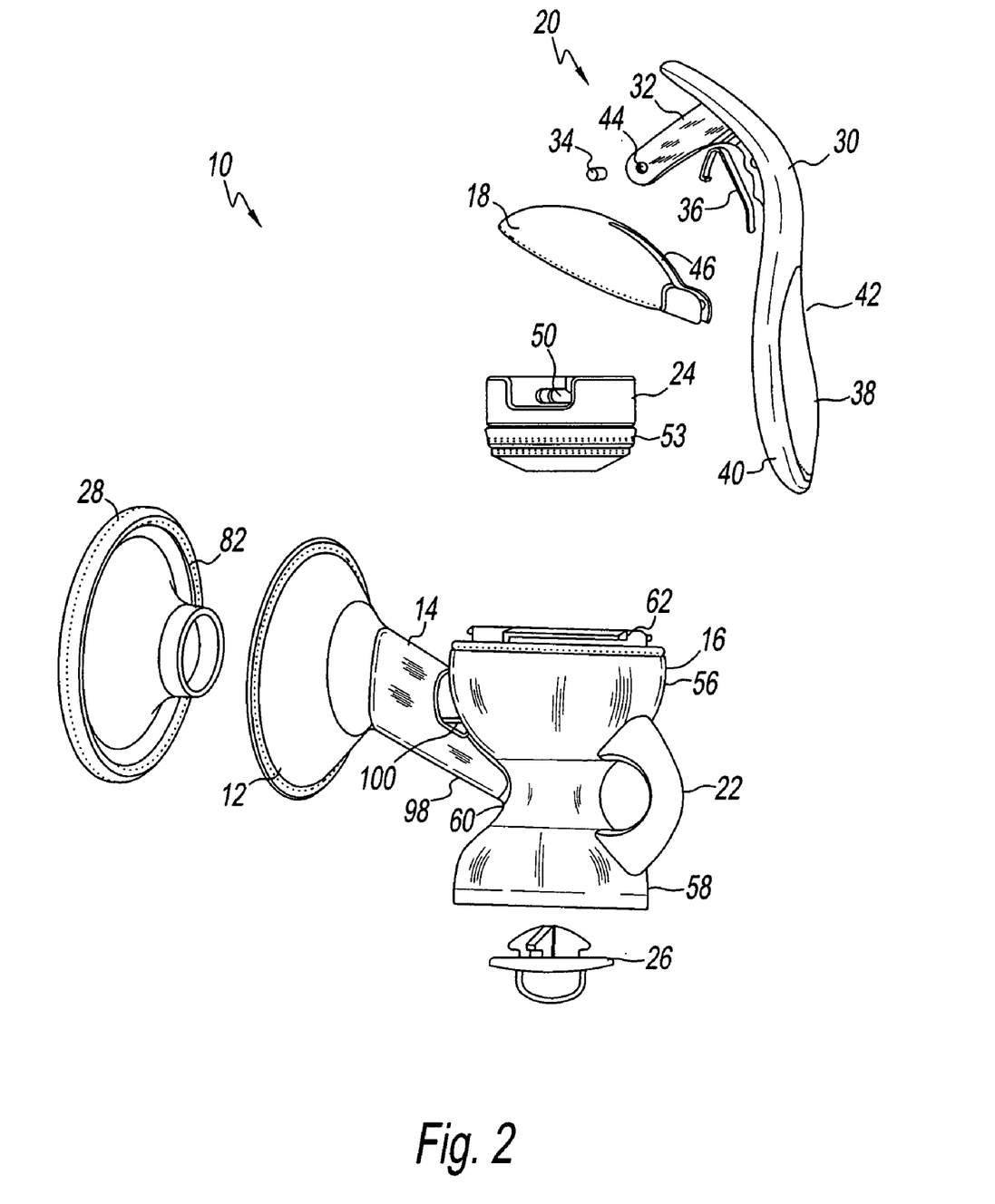
FIG. 2 is an exploded view of the manual breast pump of FIG. 1.
Figure 3:
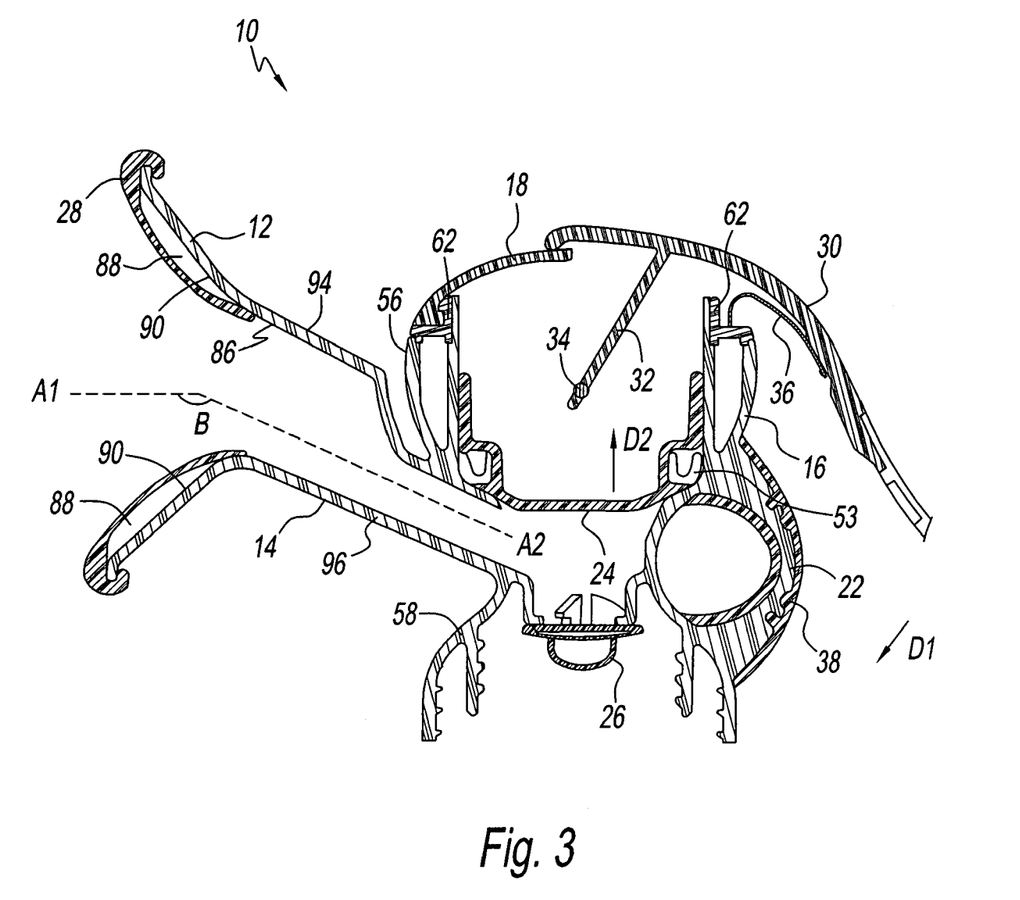
FIG. 3 is a cross sectional view of the manual breast pump of FIGS. 1 and 2, taken along line 3-3 of FIG. 1.

Referring to the drawings and in particular, to FIGS. 1 through 3, there is provided a manual breast pump generally represented by reference numeral 10. Breast pump 10 includes a cup 12, a funnel 14, a housing 16, a lid 18, a handle assembly 20 and a finger grip 22. Handle assembly 20 is pivotably connected to lid 18, and a piston 24 is connected to handle assembly 20 and movably positioned within housing 16. A valve 26 is located at a lower end of housing 16, and an insert 28 is securably positioned within cup 12. A receptacle 27 for receiving milk pumped from the breast of a user is removable connected to housing 16.

Handle assembly 20 includes handle 30, lever 32, pin 34, and spring 36. Spring 36 connects lid 18 with handle assembly 20. In the embodiment shown, handle 30 has a curved shape that narrows in width as it extends from a distal end to a proximal end with the proximal end being defined as the end near the lid of the breast pump 10. In one embodiment, portions of handle 30 include a soft material 38, such as a thermoplastic elastomer (TPE), molded over a base of rigid material 40 such as a polycarbonate resin. Soft material 38 is preferably positioned on portions of handle 30 that will come into contact with a user's hand, particularly in a top region 42 near the distal end of handle 30. Additionally, soft material 38 may be textured to provide enhanced grip and comfort during use of breast pump 10.

Lever 32 extends from handle 30 and includes an aperture 44 for securely housing pin 34. Lever 32 extends through an opening 46 in lid 18 to engage piston 24 by use of a pin 34. Piston 24 includes a channel 48 for receiving lever 32 and slots 50 for receiving pin 34. Slots 50 are formed in each of the walls that create channel 48.

Figure 4A:
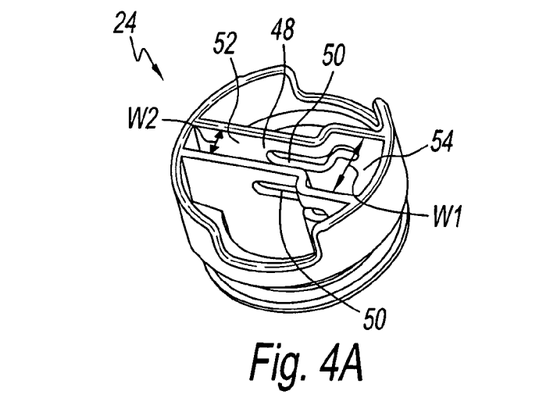
FIGS. 4A through 4C are detailed views of a piston of the manual breast pump of FIG. 1.
Figure 4B:
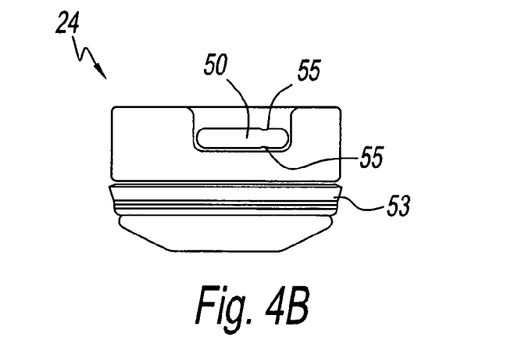
Figure 4C:
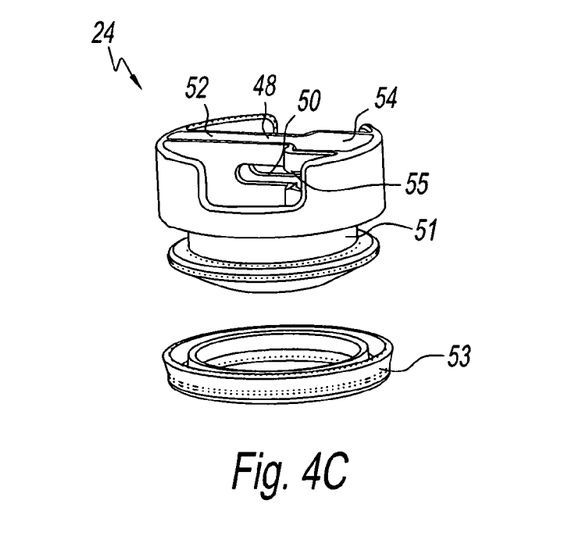

Piston 24 is shown in greater detail in FIGS. 4A through 4C. Channel 48 includes a narrow portion 52 and a wide portion 54. Preferably, wide portion 54 has a width W1 that is greater than the length of pin 34, and narrow portion 52 has a width W2 that is less than the length of pin 34. This configuration allows pin 34 to be inserted into wide portion 54 and pushed forward to slidably engage with slots 50 in narrow portion 52 of channel 48. In one embodiment, the width W1 of wide portion 54 is at least twice the width W2 of narrow portion 52. Piston 34 is engaged with handle assembly 20 by first inserting lever 32 into wide portion 54 of channel 48, and then moving lever 32 forward into narrow portion 52 of channel 48 to engage pin 34 with slots 50. Slots 50 include protrusions 55 extending into the slots to lock pin 34 in place.

Advantageously, this configuration allows piston 24 to easily be separated from handle assembly 20 and lid 18 for cleaning or other maintenance purposes. Piston 24 also includes a sealing member channel 51 for receiving a sealing member 53. Sealing member 53 is preferably a flexible, annular member with a substantially U-shaped cross section. The outside diameter of sealing member 53 is slightly larger than the outside diameter of piston 24 and substantially the same diameter as the inner diameter of housing 16 to create an airtight seal when piston 24 moves within housing 16.

In the embodiment shown in FIGS. 1 through 3, housing 16 has, as shown clearly in FIG. 2, an hourglass shape, with an upper portion 56 for receiving piston 24, a lower portion 58 for connecting to a storage receptacle, and a narrowed central portion 60. In the embodiment shown, finger grip 22 is a semicircular ring extending from upper portion 56 to lower portion 58, and is made of rigid material 40 overmolded with compliant or soft material 38. Finger grip 22 preferably has a diameter large enough to accommodate an average user's thumb. Soft material 38 may be TPE, gel, or any other material that will enhance comfort for a user. Although the finger grip 22 shown in FIGS. 1 through 3 is a semicircular ring, the present disclosure contemplates the use of any number of configurations for finger grip 22. For example, finger grip 22 may be a hook-like structure attached or connected to either upper portion 56, lower portion 58, or central portion 60 of housing 16. Alternatively, finger grip 22 could be a ledge or groove that provides sufficient area for gripping purposes.

Housing 16 includes a locking structure 62. Locking structure 62 may be integrally formed with housing 16 or may be formed separately and attached to housing 16.

Figure 5A:
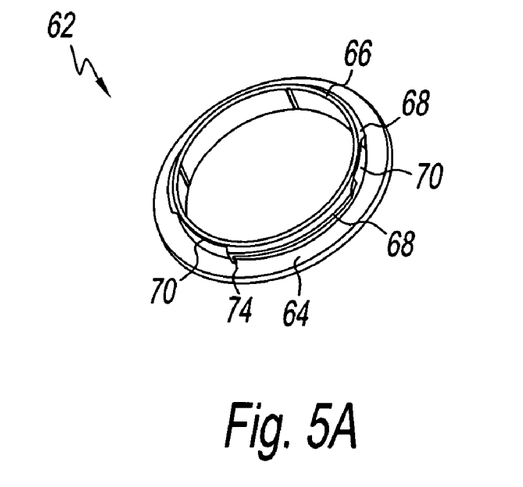
FIGS. 5A through 5C are detailed views of a locking structure of the manual breast pump of FIG. 1.
Figure 5B:
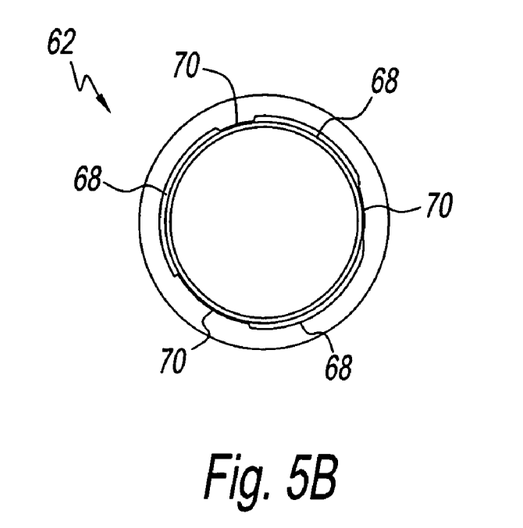
Figure 5C:
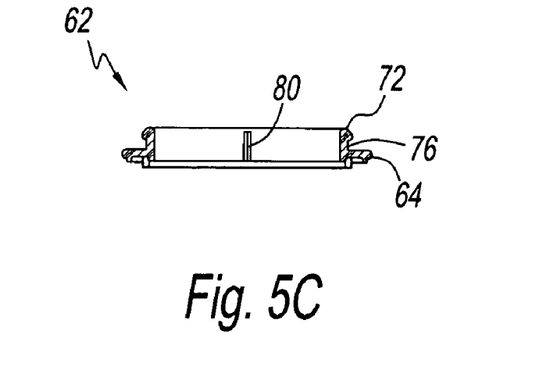

In the embodiment shown in FIGS. 1 through 3, locking structure 62 includes an annular structure having a base 64 with side walls 66 extending upward from the base. Preferably, locking structure 62 is permanently attached to upper portion 56 of housing 16 by a welding or gluing process. Details of locking structure 62 are shown in FIGS. 5A through 5C. Side walls 66 of locking structure 62 have two or more locking members 68 with openings 70 between locking members 68. Each locking member 68 includes an upper portion 72 and a stopper 74. Upper portions 72 of locking members 68 are substantially parallel to base 64, forming grooves 76.

Figure 6A:
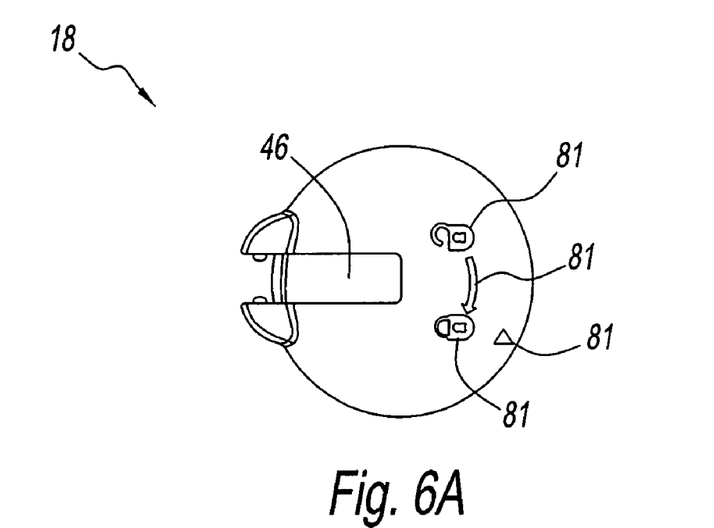
FIGS. 6A and 6B are detailed views of a lid of the manual breast pump of FIG. 1.
Figure 6B:
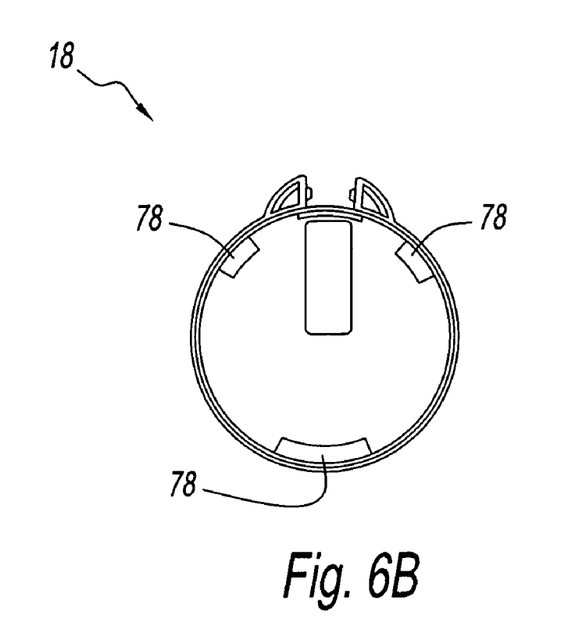

Details of lid 18 are shown in FIGS. 6A and 6B. Lid 18 includes two or more tabs 78. Tabs 78 are sized such that the tabs correspond to the openings 70 between locking members 68. To removably secure lid 18 to locking structure 62, tabs 78 of lid 18 are inserted into grooves 76 via openings 70 between locking members 68. Lid 18 is then rotated in such a way that tabs 78 move within grooves 76 until tabs 78 abut stoppers 74, locking lid 18 in place on top of housing 16. In the embodiment shown in the drawings, side walls 66 also include two or more protrusions 80. Protrusions 80 serve to help hold lid 18 in place and prevent accidental unlocking of the lid. In the embodiment shown, lid 18 and housing 16 include graphics 81 indicating a locked and an unlocked position of the lid. Preferably, graphics 81 are textured graphics integrally formed on housing 16 and lid 18.

Figure 7A:
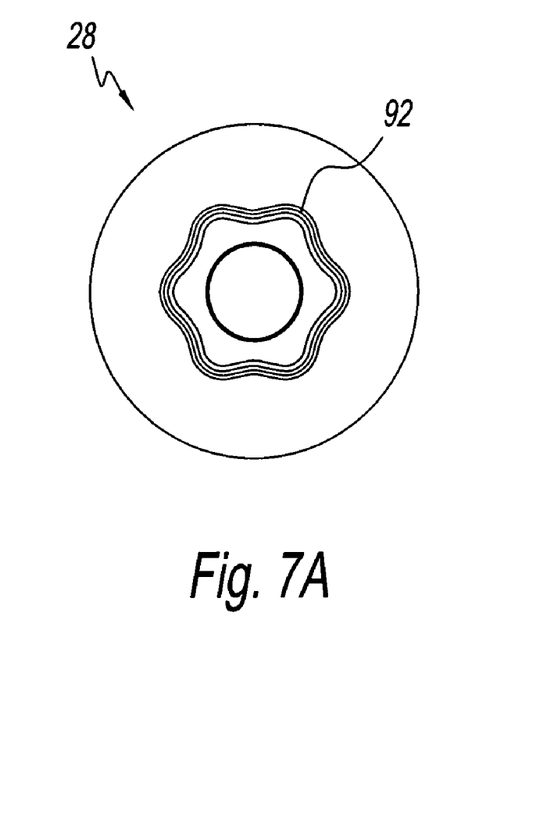
FIGS. 7A and 7B are detailed views of an insert for use with the cup of the manual breast pump of FIG. 1.
Figure 7B:
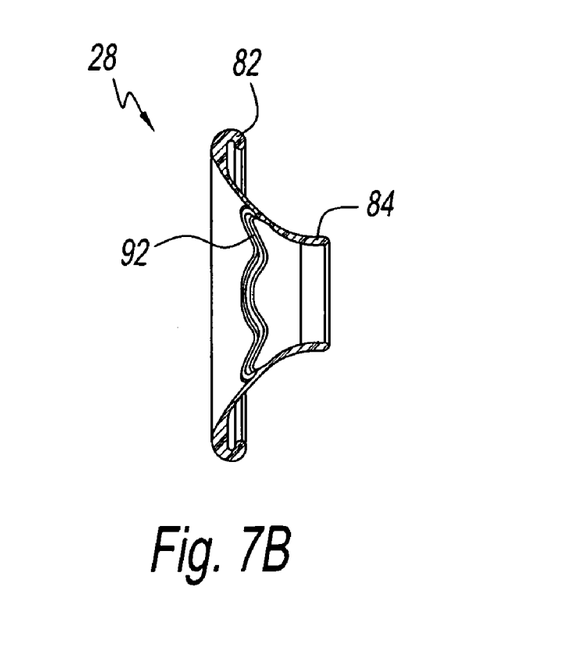

FIGS. 7A and 7B show details of insert 28. Insert 28 is preferably made of a flexible material, such as silicone. Insert 28 sealingly connects with cup 12 along a periphery of the cup. In one embodiment, insert 28 includes a lip 82 that connects to the periphery of cup 12. Insert 28 also has neck 84 that abuts against an inner surface 86 of funnel 14. When insert 28 is connected to cup 12, an air volume 88 is formed between an insert 28 and an inner surface 90 of cup 12. Air volume 88 is an isolated air volume. In other words, lip 82 and neck 84 of insert 28 create an air tight seal with cup 12, forming an air volume 88 that is in fluid isolation from any other air volume, including the ambient air and the air within housing 16, funnel 14, and cup 12. During operation of breast pump 10, air volume 88 expands and contracts due to pressure differences caused by the movement of piston 24 within housing 16. As a result, insert 28 moves with respect to cup 12, providing a massaging action to the breast of the user. Insert 28 also includes a massaging projection 92. In the embodiment shown in FIGS. 7A and 7B, massaging projection 92 is a continuous undulated ridge that has an overall star-like shape. However, any number of other shapes and types of projections are contemplated by the present disclosure. Massaging projection 92 increases the effectiveness of the massaging action and makes the breast pump 10 more comfortable to use.

Referring to FIG. 3, cup 12 is substantially frusto-conical in shape and substantially centered about an axis A1. Funnel 14 has an upper portion 94 that is substantially cylindrical in shape and substantially centered about an axis A2. Funnel 14 also includes a lower portion 96, having a curved lower surface 98 and a flat upper surface 100. An angle B is formed between axis A1 and axis A2. Most preferably, angle B is between approximately 90° and approximately 178°. Preferably, angle B is between approximately 115° and 165°. In one preferred embodiment, angle B is approximately 160°. Positioning funnel 14 at an angle B with respect to cup 12 allows a user to pump in a more comfortable position, because milk naturally flows down funnel 14 toward valve 26 and into receptacle 27. This prevents a user from having to lean forward while pumping. The angling of cup 12 with respect to funnel 14 also helps prevent the back flow of milk during use of breast pump 10.

Valve 26 is preferably a one-way valve positioned in the pump housing to allow flow of breast milk from funnel 14 into receptacle 27. Receptacle 27 may be a bottle, liner or holder with a liner, or any other suitable container. Housing 16 may include two or more concentric threads allowing housing 16 to be connected to various sizes of receptacles 27. In the embodiment shown in FIGS. 1 through 3, the valve 26 is a plug valve. However, the present disclosure contemplates the use of other types of valves and/or barriers that allow for the flow of the breast milk into receptacle 27 while preventing back-flow of the milk into funnel 14. In one embodiment, valve 26 is made from a colorful material to aid in locating the valve when it is disassembled from breast pump 10. For example, rather than being transparent, valve 26 may be blue in color, allowing a user to more easily locate valve 26 when the valve is being washed in a sink or dishwasher. Other colors and/or multiple colors for valve 26 are also contemplated by the present disclosure.

The flexible insert is preferably transparent and has a color, such as, for example, blue, which allows a user to more easily see the pumping and/or massaging action during operation. Other colors and/or structures can also be used as an indicator of pumping operation.

In operation, cup 12 receives a user's breast, and insert 28 forms a seal surrounding the nipple of the breast. Movement of handle assembly 20 causes piston 24 to move reciprocally within housing 16, which creates a negative pressure on the breast, facilitating the expression of milk. As handle 30 is moved in direction D1 as shown in FIG. 3, lever 32 and pin 34 cause piston 24 to move upward in direction D2, creating a negative pressure that tends to pull the nipple toward funnel 14, causing milk to be expressed from the breast. At the same time, air volume 88 expands due to the pressure differential. As air volume 88 expands, insert 28 and massaging projection 92 push against the breast to provide a massaging action, which further aids in the expression of milk from the breast, and enhances comfort for a user. When handle 30 is released, spring 36 causes handle assembly 20 and piston 24 to return to their initial positions as shown in FIG. 3.

Previous manual breast pumps cannot comfortably be used by women having small hands. Advantageously, breast pump 10 includes finger grip 22, which allows breast pump 10 to be used comfortably by a wide variety of users. Finger grip 22 on breast pump 10 especially allows users with small hands to comfortably use breast pump 10. For example, to operate breast pump 10, a user may place her thumb of one hand in finger grip 22 and pull handle 30 toward finger grip 22 using one or more fingers from the same hand. Alternatively, a user may place a finger in finger grip 22 and use the thumb or another part of the hand to pull handle 30 toward the finger grip.

Finger grip 22 also provides for reduced noise and vibration of breast pump 10. During use of breast pump 10, handle 30 is pulled toward, and comes into contact with, finger grip 22. Thus, finger grip 22 prevents handle 30 from contacting the housing 16 or receptacle 27. Finger grip 22 is overmolded with a soft material, and it has been found that the use soft material on finger grip 22 significantly reduces the noise and vibration produced by breast pump 10 when in use.

Figure 8A:
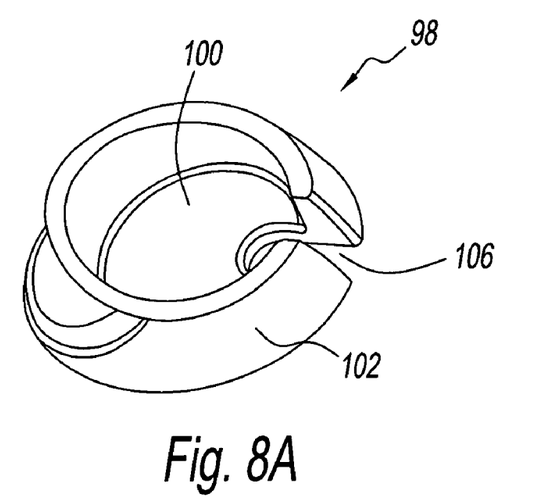
FIGS. 8A through 8C are detailed views of a stand for use with the manual breast pump of FIG. 1.
Figure 8B:
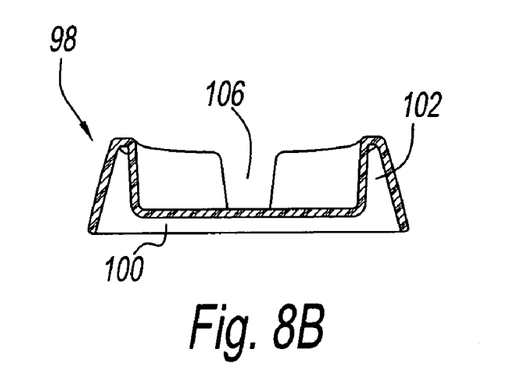
Figure 8C:
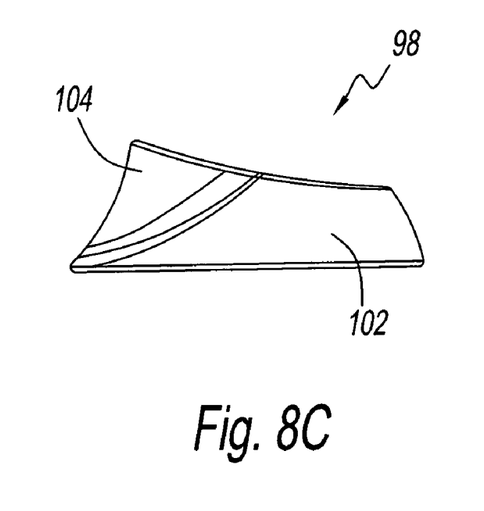

FIGS. 8A through 8C show a stand 98 for use with breast pump 10. Stand 98 has a base 100 and a wall 102. Stand 98 can receive receptacle 27. Wall 102 has an elevated portion 104 for supporting receptacle 27. Stand 98 also has a cut-out 106 extending through base 100 and wall 102. Cut-out 106 adds flexibility for insertion and removal of receptacle 27.

While the present disclosure has been described with reference to one or more exemplary embodiments, it will be understood by those skilled in the art that various changes may be made and equivalents may be substituted for elements thereof without departing from the scope of the present disclosure. In addition, many modifications may be made to adapt a particular situation or material to the teachings of the disclosure without departing from the scope thereof. Therefore, it is intended that the present disclosure not be limited to the particular embodiment(s) disclosed as the best mode contemplated, but that the disclosure will include all embodiments falling within the scope of the appended claims.

The invention claimed is:

1. A manual breast pump comprising:
a housing;
a cup for receiving a breast;
a funnel connecting the cup to the housing to form a passage for breast milk;
a piston within an interior volume of the housing;
a movable handle connected to the housing; and
a lever that removably connects the piston to the movable handle, the lever having a proximal end and a distal end, the lever being connected to the movable handle at the proximal end and connected to a pin protruding outward from the lever at the distal end, the pin having a first end and a second end opposite the first end, the piston having a first side wall with a first slot formed therethrough and a second side wall with a second slot formed therethrough, wherein the first end of the pin passes through the first slot, and wherein the second end of the pin passes through the second slot thereby removably connecting the piston to the lever.

2. The manual breast pump of claim 1, wherein the piston moves reciprocally within the housing to create a negative pressure for the expression of breast milk from the breast.

3. The manual breast pump of claim 2, wherein the first side wall and the second side wall form a channel.

4. The manual breast pump of claim 3, wherein the channel comprises a wide portion and a narrow portion.

5. The manual breast pump of claim 3, wherein the piston comprises a base connected to and surrounded by a piston wall that is connectable to a sealing member, and wherein the first side wall and the second side wall are connected within the piston wall so that at least a portion of both the first side wall and the second sidewall are parallel to form the channel therebetween.

6. The manual breast pump of claim 5, wherein the first wall and the second wall are spaced at a first distance forming a narrow portion along a first length of the channel and spaced at a second distance forming a wide portion along a second length of the channel, and wherein the wide portion has a width greater than a length of the pin and the narrow portion has a width that is less than a length of the pin, wherein the pin is inserted into the wide portion and pushed forward to slidably engage with the first slot in the first wall and the second slot in the second wall in the narrow portion of the channel.

7. The manual breast pump of claim 4, wherein the wide portion has a first width that is greater than a length of the pin and the narrow portion has a second width that is less than the length of the pin.

8. The manual breast pump of claim 7, wherein the first width is at least twice as wide as the second width.

9. The manual breast pump of claim 1, wherein the housing has an hour glass shape with an upper portion, a lower portion, and a narrowed central portion, and wherein the housing has a finger grip that extends from the upper portion to the lower portion.

10. The manual breast pump of claim 1, further comprising a finger grip connected to the housing that is separate from the movable handle, wherein the finger grip comprises a compliant material.

11. The manual breast pump of claim 10, wherein the compliant material is selected from the group consisting of a thermoplastic elastomer, a gel material, a textured material, and any combinations thereof.

12. The manual breast pump of claim 1, wherein the housing further comprises a locking structure for removably connecting a lid to the housing.

13. The manual breast pump of claim 12, wherein the lid is movable between a locked position and an unlocked position.

14. The manual breast pump of claim 13, further comprising graphical indicators on the lid, wherein the graphical indicators indicate whether the lid is in the unlocked or the locked position.

15. The manual breast pump of claim 1, wherein the cup is centered about a first axis, the funnel is centered about a second axis, and wherein the first axis forms an angle with the second axis.

16. The manual breast pump of claim 15, wherein the angle between the first axis and the second axis is between approximately 90° and approximately 178°.

17. The manual breast pump of claim 15, wherein the angle between the first axis and the second axis is between approximately 115° and approximately 165°.

18. The manual breast pump of claim 15, wherein the angle between the first axis and the second axis is approximately 160°.

19. The manual breast pump of claim 1, further comprising a stand for receiving the receptacle, wherein the stand comprises a base and a wall having a cut-out extending through the base and the wall.

20. A manual breast pump comprising:
 a housing having an interior volume;
 a funnel connected to the housing to form a passage for breast milk;
 a cup for receiving a breast, the cup being connected to the funnel;
 a piston in the interior volume;
 a flexible insert sealably secured to the cup and funnel so that an isolated air volume is formed between the cup and the flexible insert, the cup having an inner surface in the isolated air volume, said flexible insert having a first end, a second end opposite the first end, and a flexible wall therebetween, the first end of the flexible insert being secured to the cup and the second end of the flexible insert being connected to the funnel, the inner surface of the cup being continuous in the isolated air volume so that the isolated air volume is in fluid isolation from ambient air and air in the housing, the funnel and the cup, wherein the isolated air volume expands and contracts as the piston moves reciprocally in the housing, to cause the flexible insert to move.

21. The manual breast pump of claim 20, further comprising a receptacle for receiving the breast milk, the receptacle being removably connected to a lower portion of the housing.

22. The manual breast pump of claim 20, wherein the flexible insert further comprises a massaging projection.

23. The manual breast pump of claim 22, wherein the massaging projection comprises a continuous undulated ridge.

24. The manual breast pump of claim 20, further comprising a stand for receiving the receptacle, wherein the stand comprises a base and a wall having an inner surface facing a space that receives the receptacle and an outer surface opposite the inner surface, and wherein the stand has a cut-out extending through the base and the inner surface and outer surface of the wall.

25. The manual breast pump of claim 20, wherein during operation of the manual breast pump, the isolated air volume expands and contracts due to pressure differences caused by movement of the piston within the housing to move the flexible wall with respect to the cup.

* * * * *